(12) United States Patent
Burke et al.

(10) Patent No.: US 8,988,235 B2
(45) Date of Patent: Mar. 24, 2015

(54) FORCE INDICATING ATTACHMENT STRAP FOR AN ORTHOTIC

(75) Inventors: Steven Burke, Huntington Beach, CA (US); Geoffrey Garth, Long Beach, CA (US); Jozsef Horvath, Fullerton, CA (US)

(73) Assignee: Aspen Medical Partners, LLC, Irvine, CA (US)

( * ) Notice: Subject to any disclaimer, the term of this patent is extended or adjusted under 35 U.S.C. 154(b) by 950 days.

(21) Appl. No.: 13/092,393

(22) Filed: Apr. 22, 2011

(65) Prior Publication Data

US 2012/0268284 A1    Oct. 25, 2012

(51) Int. Cl.
| | |
|---|---|
| *G08B 21/00* | (2006.01) |
| *A61F 5/00* | (2006.01) |
| *G09B 21/00* | (2006.01) |
| *H04B 3/36* | (2006.01) |
| *A61F 5/055* | (2006.01) |
| *A61F 5/01* | (2006.01) |
| *A61F 5/02* | (2006.01) |

(52) U.S. Cl.
CPC . *A61F 5/055* (2013.01); *A61F 5/01* (2013.01); *A61F 5/02* (2013.01)
USPC ............... 340/668; 602/5; 602/18; 340/675; 340/686.1; 340/4.12; 340/407.1; 116/212; 24/68 R

(58) Field of Classification Search
CPC ....... B60N 2/2806; B60R 22/105; G01L 1/02
USPC ................. 340/668, 675, 686.1, 4.12, 407.1; 602/18, 5, 201–203, 16, 20, 23, 26; 116/212; 24/593.1, 591.1, 68
See application file for complete search history.

(56) References Cited

U.S. PATENT DOCUMENTS

| | | | | |
|---|---|---|---|---|
| 2,100,649 | A | * | 11/1937 | Mossberg .......................... 42/126 |
| 4,300,129 | A | * | 11/1981 | Cataldo ..................... 340/539.11 |
| 4,832,410 | A | | 5/1989 | Bougher |
| 5,121,747 | A | * | 6/1992 | Andrews ............................ 607/2 |
| 5,306,230 | A | | 4/1994 | Bodine |
| 5,503,620 | A | | 4/1996 | Danzger |
| 5,522,401 | A | * | 6/1996 | Brucker ......................... 600/594 |
| 7,242,286 | B2 | | 7/2007 | Knox |
| 7,285,103 | B2 | | 10/2007 | Nathanson |
| 7,993,292 | B2 | * | 8/2011 | Sterling et al. .................. 602/13 |
| 8,593,293 | B2 | * | 11/2013 | Harrison et al. .............. 340/668 |

(Continued)

FOREIGN PATENT DOCUMENTS

| | | |
|---|---|---|
| EP | 1723012 | 10/2008 |
| WO | 2005/059493 | 6/2005 |

(Continued)

OTHER PUBLICATIONS

"Click & Safe—Britax USA", http://www.britaxusa.com/learning-center/superior-ease-of-use/click-and-safe, Copyright 2008 Britax USA.

*Primary Examiner* — Benjamin C Lee
*Assistant Examiner* — Sigmund Tang
(74) *Attorney, Agent, or Firm* — Fish & Tsang LLP

(57) ABSTRACT

An improved orthotic has a strap that secures the orthotic to a wearer, and comprises a tension indicator coupled to the strap. The tension indicator includes a first element disposed to produce a tactile signal when a tension in the strap reaches a threshold that is less than a permanent deformation threshold.

8 Claims, 9 Drawing Sheets

(56) References Cited

U.S. PATENT DOCUMENTS

| | | | |
|---|---|---|---|
| 2003/0139766 A1* | 7/2003 | McEwen et al. | 606/203 |
| 2004/0011277 A1* | 1/2004 | Barnes et al. | 116/202 |
| 2005/0278902 A1* | 12/2005 | Wilcox et al. | 24/68 CD |
| 2005/0280297 A1* | 12/2005 | Patterson et al. | 297/217.4 |
| 2007/0068282 A1 | 3/2007 | Nakagawa et al. | |
| 2008/0072404 A1* | 3/2008 | Wetter | 24/68 R |
| 2010/0007186 A1* | 1/2010 | Strong et al. | 297/250.1 |
| 2012/0071917 A1* | 3/2012 | McDonald et al. | 606/203 |

FOREIGN PATENT DOCUMENTS

| | | |
|---|---|---|
| WO | 2005/067825 | 7/2005 |
| WO | 2005/092676 | 10/2005 |
| WO | 2006/059114 | 6/2006 |
| WO | 2007/060417 | 5/2007 |
| WO | 2007/129079 | 11/2007 |

\* cited by examiner

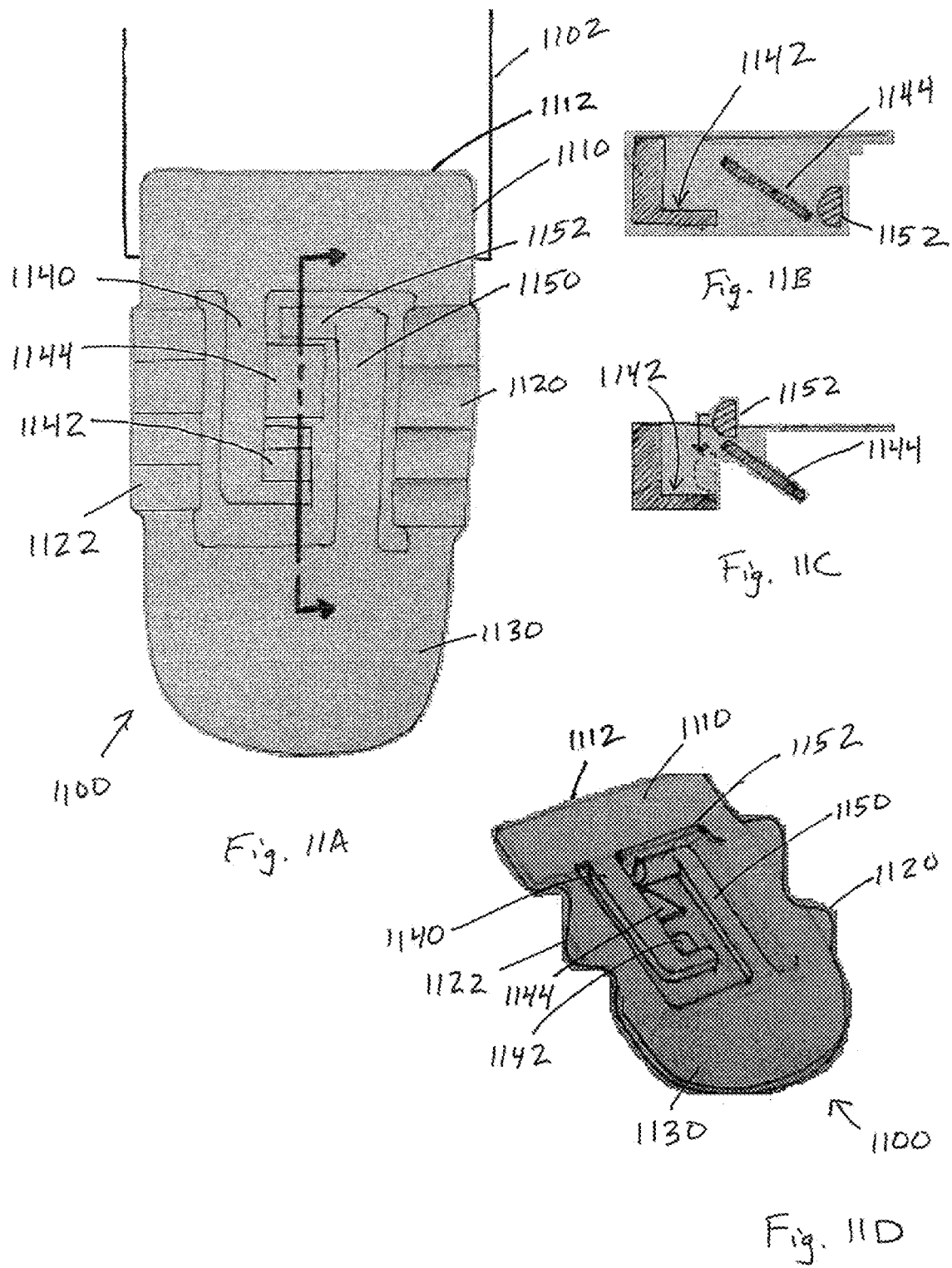

FORCE INDICATING ATTACHMENT STRAP FOR AN ORTHOTIC

FIELD OF THE INVENTION

The field of the invention is orthotics.

BACKGROUND

It is generally known to include visual tension indicators with orthotics that indicate when a proper closure force is applied to the orthotics to ensure the best outcomes for fit and function. For example, a collar with too much force applied could cause reduced blood flow or discomfort, while a collar without sufficient force applied could improperly support the neck and in addition, could lead to skin breakdown.

For example, U.S. Pat. No. 285,103 to Nathanson and WIPO Publ. No. 2005/092676 to Wetter (publ. Oct. 6, 2005) discuss an example of a visual tension indicator disposed on a strap of an orthotic. The tension indicator uncovers differently colored sections depending on whether or not a proper tension is applied. Another example of a visual tension indicator is discusses in U.S. Pat. No. 5,503,620 to Danzger, in which a back support has an elastic indicator band that operates to show when the belt is properly tensioned.

Nathanson, Danzger, and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

It is also known to use visual tension indicators with seat belts, such as that described in European Patent No. 1723012 to Wetter. However, the visual tension indicator discussed in Wetter suffers from the same disadvantages discussed above.

Visual tension indicators can be problematic, as the visual signals produced by the tension indicators are often difficult (if not impossible) for wearers of the orthotics to see, and therefore require others to assist in properly tensioning the orthotics to the wearers. For example, when the Danzger support belt is worn, the tension indicator disposed on the belt is located at the wearer's lower back and out of the wearer's line-of-sight. Such problems are exacerbated for orthotic wearers having partial or total vision loss.

To provide a non-visual indication of the tension within a strap, it is known to utilize electronic tension indicators in conjunction with a seat belt that produce an audible alert. Examples are discussed in U.S. Pat. No. 7,242,286 to Knox, WIPO Publ. No. 2005/059493 to Miller, et al. (publ. Jun. 30, 2005), WIPO Publ, No. 2006/059114 to Carine (publ. Jun. 8, 2006, and WIPO Publ. No. 2007/060417 to Carine (publ. May 31, 2007). However, such audible tension indicators can be problematic as they require power and electronic circuitry to function. In addition, the added complexity of the electronic indicators often leads to malfunctions or other problems not experienced when using mechanical indicators.

In an attempt to avoid many of the disadvantages discussed above, WIPO Publ. No. 2007/129079 to Harrison, et al. (publ, Nov. 15, 2007) discusses a tension indicator that produces an audible signal when a tension in the strap reaches a predetermined value, and without the need for electronics. One problem with the Harrison indicator is that the indicator must not move with the strap, but rather be fixed in place while the strap moves.

Thus, there is still a need for an orthotic having a tension indicator that provides a tactile indication when a proper tension is applied to the orthotic's strap.

SUMMARY OF THE INVENTION

The inventive subject matter provides apparatus, systems and methods in which a strap of an orthotic comprises a first tension indicator disposed on the strap such that a tactile signal is produced when a tension in the strap reaches a first threshold. As used herein, "signal" means an indication discernible by a human, and "tactile signal" means a signal perceptible to the sense of touch, such as a momentary change in pressure or vibration on the skin, but does not include the ability to feel tension in a strap such as by manipulating (e.g., twisting) the strap. As used herein, "audible signal" means some sort of audible sound, such as a momentary click or popping noise.

Contemplated thresholds discussed herein are less than a permanent deformation threshold of the strap or orthotic device. As used herein, "permanent deformation threshold" means an amount of force beyond which the strap or orthotic device is permanently deformed, such as beyond the yield point on a stress-strain curve. All commercially-suitable orthotics are contemplated including, for example, braces, shoes, and other medical devices designed to support, straighten, and/or improve the function of one or more areas of the wearer's body.

As used herein, "strap" means an elongated strip distinct from the tension indicator, which is coupled to an orthotic and used to secure and tension the orthotic to a wearer. Preferred straps are inelastic, although at least partially elastic straps could also be used. As used herein, "elastic" means having a non-permanent deformation upon a longitudinal stretching of at least 10%. Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

In some contemplated embodiments, the tension indicator can deform as tension in the strap increases, and can cause a tactile signal to be produced when the tension in the strap reaches or exceeds a defined amount. It is further contemplated that the deformation of the tension indicator can be temporary, and when the tension in the strap is decreased, the tension indicator can revert to an initial or non-deformed state.

In other contemplated embodiments, the tension indicator can be disposed on the strap such that the tension indicator interacts with a member of the orthotic when the tension in the strap reaches or exceeds a defined amount. The resulting interaction between the indicator and the member produces a tactile signal. Typically, such signal is produced when a proper amount of tension has been applied to the strap.

In one aspect, methods are disclosed of producing a tactile signal to indicate that a proper level of tension in an orthotics strap. In such methods, an orthotic having a strap is provided, and a tension indicator is coupled to the strap such that at least one of a tactile signal is produced when tension in the strap reaches a threshold less than a permanent deformation threshold.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 11A is a top view of yet another embodiment of a tension indicator.

FIGS. 11B-11C are vertical cross-sectional views of the tension indicator of FIG. 11A, and FIG. 11D is a perspective view of the tension indicator of FIG. 11A.

DETAILED DESCRIPTION

Figure 1:
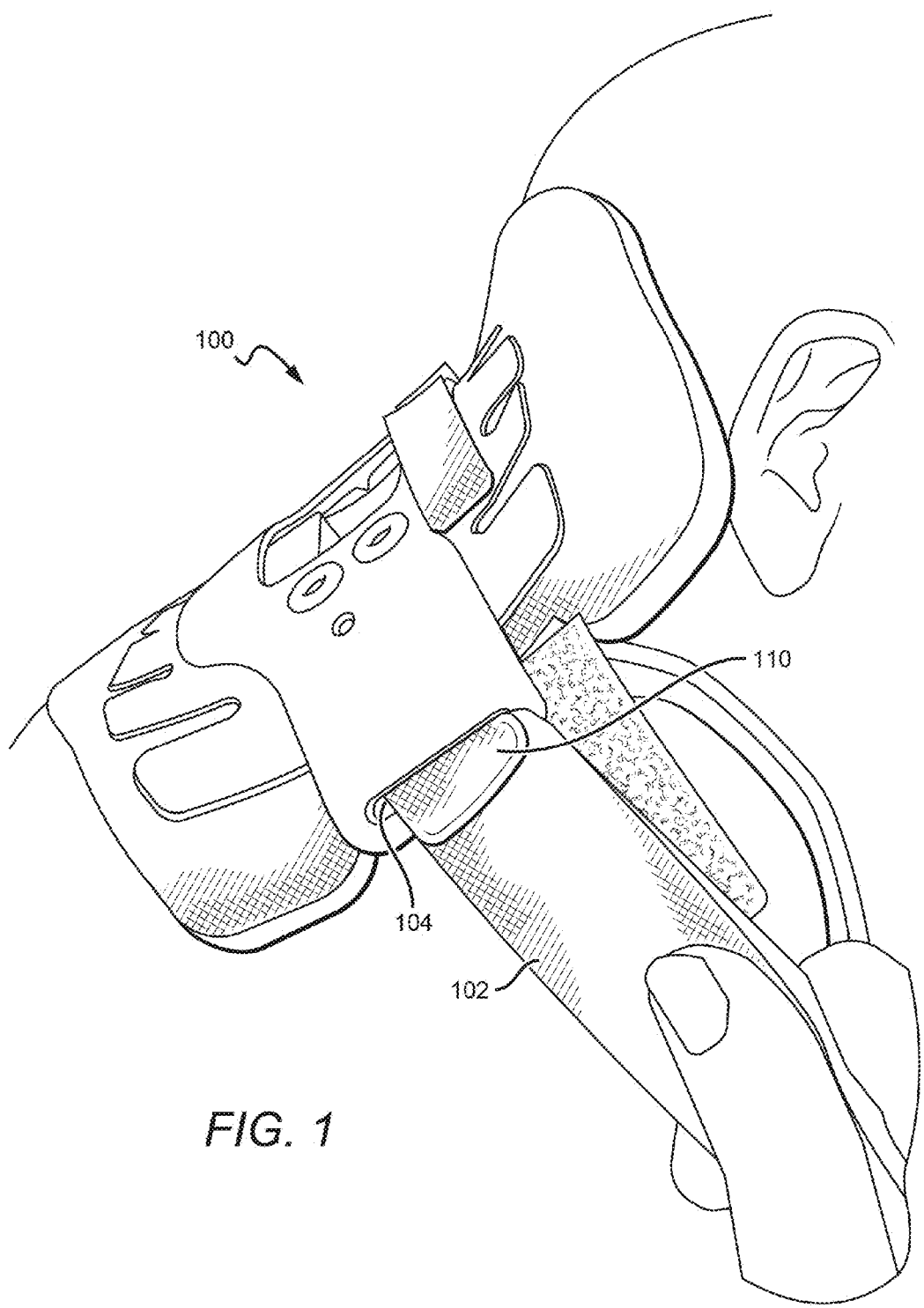
FIG. 1 is a perspective view of a tension indicator prior to the tension in the strap reaching a threshold force.

In FIG. 1, an orthotic 100 is shown having a strap 102 that tensions and secures the orthotic 100. A tension indicator 110 is coupled to the strap 102 such that a tactile signal is produced when a tension in the strap 102 reaches a threshold that is less than a permanent deformation threshold. Additional tension indicators can be coupled to the strap such that an additional tactile signal or an audible signal could be produced when tension in the strap reaches one or more defined thresholds.

Contemplated tension indicators could comprise any commercially-suitable configurations such that a signal is produced when tension in the strap reaches a first threshold. Preferred tension indicators comprise one or more preferably raised elements coupled to the strap, which are sized and dimensioned such that a tactile signal can be produced when the raised element interacts with a member of the orthotic. One preferred member is an eyelet through which the strap can pass.

Preferred elements are elastic, and can be composed of any commercially-suitable material(s) including, for example, plastics and other polycarbonates, rubbers, and any combination(s) thereof.

Persons of ordinary skill in the art will undoubtedly understand that the threshold amount of tension needed to produce the signal will vary depending on the orthotic's function and the specific needs of the orthotic's wearer. Thus, for example, the threshold tension for a neck brace would likely be different from the threshold tension for a diabetic shoe. Similarly, a lesser force would likely be necessary to properly fit a pediatric collar than that of an adult collar.

Figure 2:
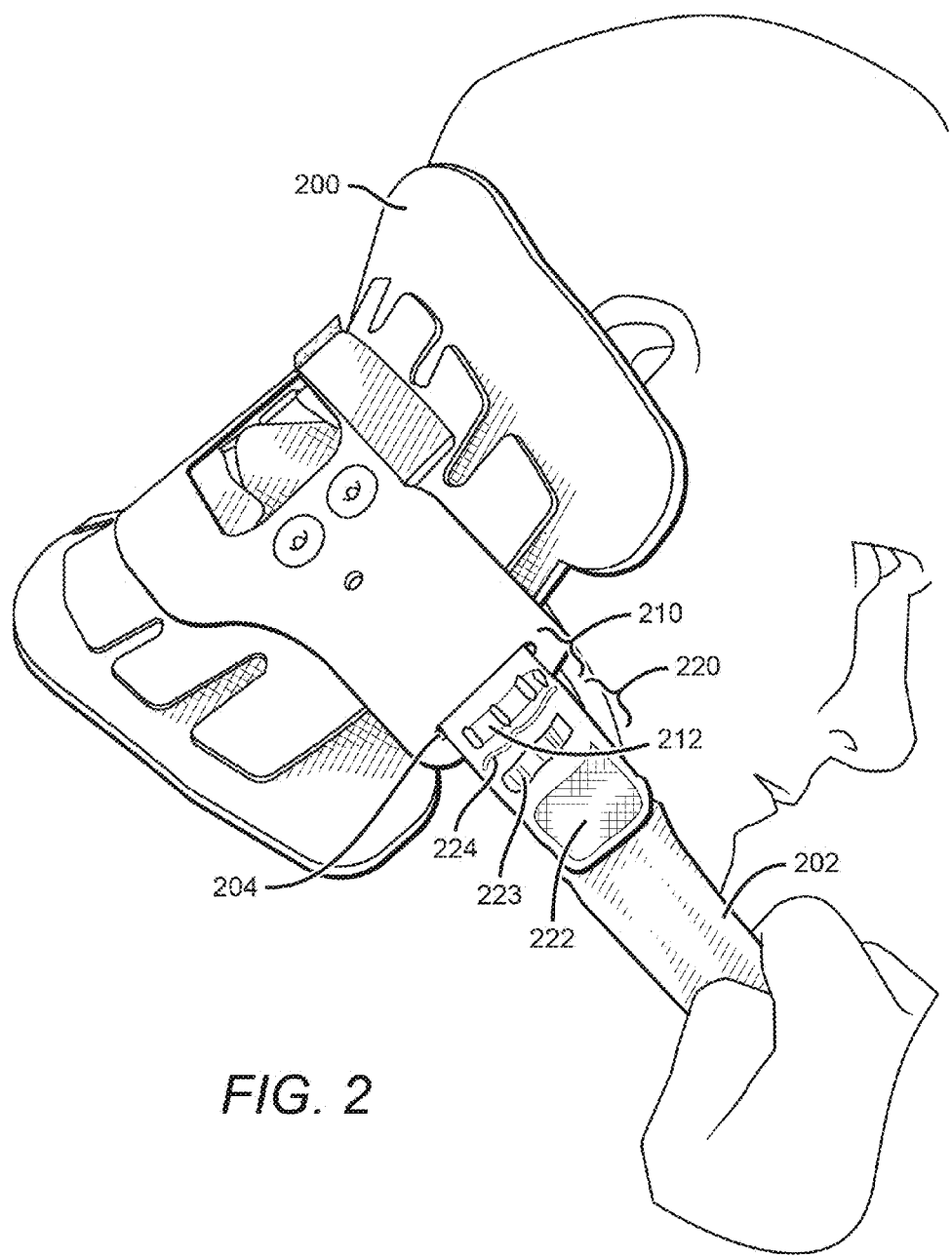
FIG. 2 is a perspective view of the tension indicator after the tension in the strap has reached a threshold force.

FIG. 2 illustrates another embodiment of an orthotic 200, which has a strap 202 that tensions and secures the orthotic 200 to a wearer. Preferred straps are inelastic, although at least partially elastic straps are also contemplated. Strap 202 can be fed through an eyelet 204 of the orthotic 200.

A first tension indicator 210 can be disposed on the strap 202 such that a first tactile signal is produced when a tension in the strap 202 reaches a first threshold. The first tension indicator 210 preferably comprises a raised element 212, which is shown in a position where tension in the strap 202 has surpassed the first threshold.

Although the raised element 212 could be of any commercially-suitable size and dimension, raised element 212 is preferably sized and dimensioned to pass through eyelet 204 with a measured resistance, such that the interaction of the raised element 212 and eyelet 204 produces the first tactile signal. The raised element 212 is preferably disposed on strap 202 such that the raised element 212 passes through eyelet 204 when tension in the strap 202 reaches the first threshold.

The tension indicator 210 can advantageously have a signal state and a non-signal state, and can revert to the non-signal state once the load is removed. This resiliency of the tension indicator 210 allows the tension indicator 210 to be reused, such that a wearer could remove orthotic 200 and then re-secure the orthotic 200 with a proper amount of tension.

As used herein, "signal state" means the shape and other configuration during and immediately following the tension indicator producing the tactile and/or audible signal. "Non-signal state" means the shape and other configuration of the indicator prior to producing the tactile and/or audible signal. Thus, for example, the tension indicator 210 is in its non-signal state prior to the tension in the strap 202 reaching a threshold amount, and once the amount of tension reaches the threshold, the tension indicator 210 produces the tactile signal and changes to its signal state.

It is contemplated that the first tension indicator 210 could alternatively be configured to produce the tactile signal when the tension in the strap 202 reaches the first threshold, and produce an audible signal when the tension in the strap 202 reaches a second threshold. However, in still other embodiments, the tension indicator 210 could produce both the tactile signal and the audible signal, either simultaneously or within a period of 1 second, when tension in the strap 202 reaches the first threshold.

A second tension indicator 220 distinct from the first tension indicator 210 can also be coupled to strap 202 such that a visual signal is produced when the tension in the strap 202 reaches a second threshold. Such threshold amount could be equal to or different from the first threshold. As used herein, "visual signal" means a visual difference in appearance, perceptible by the human eye, including for example, different color(s), different design(s), distortions of colors, designs, or shapes, and any combination(s) thereof.

Figure 5:
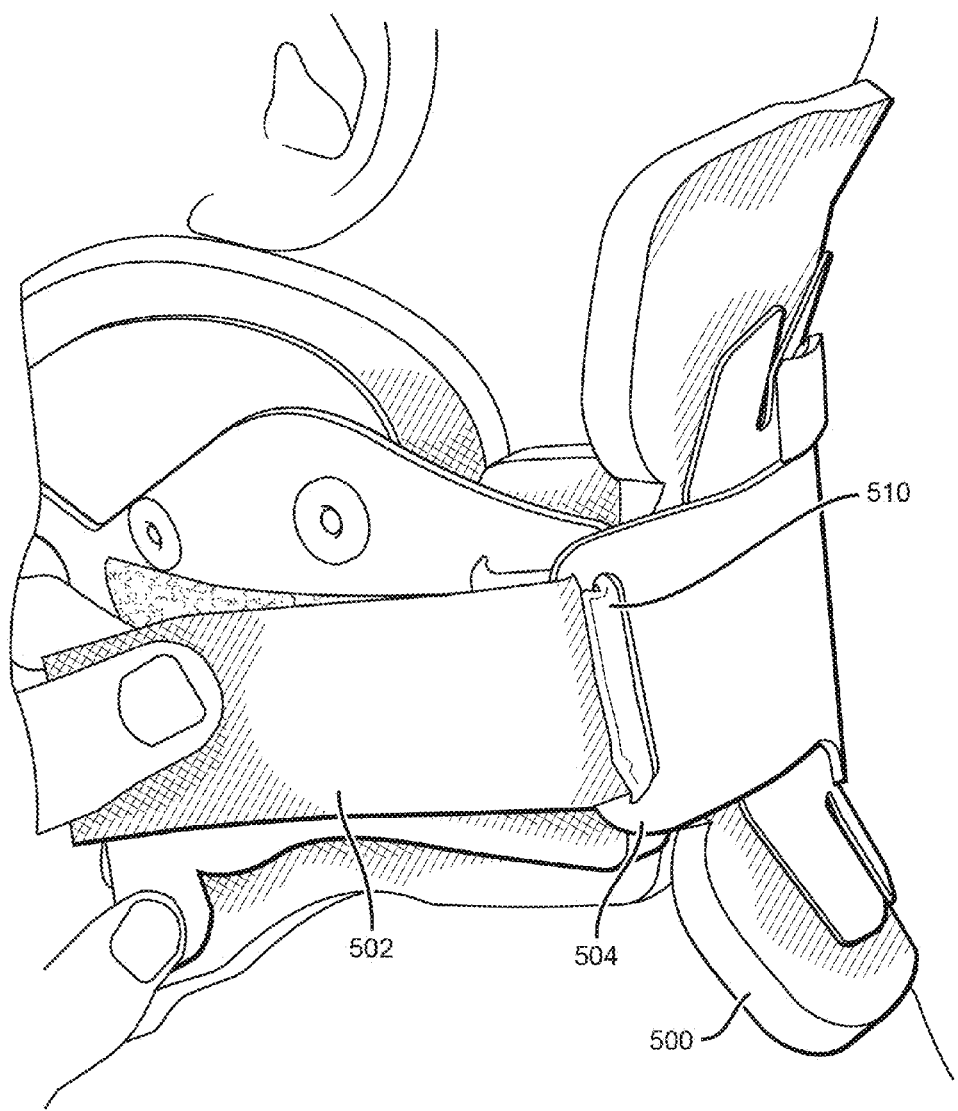
Figure 6:
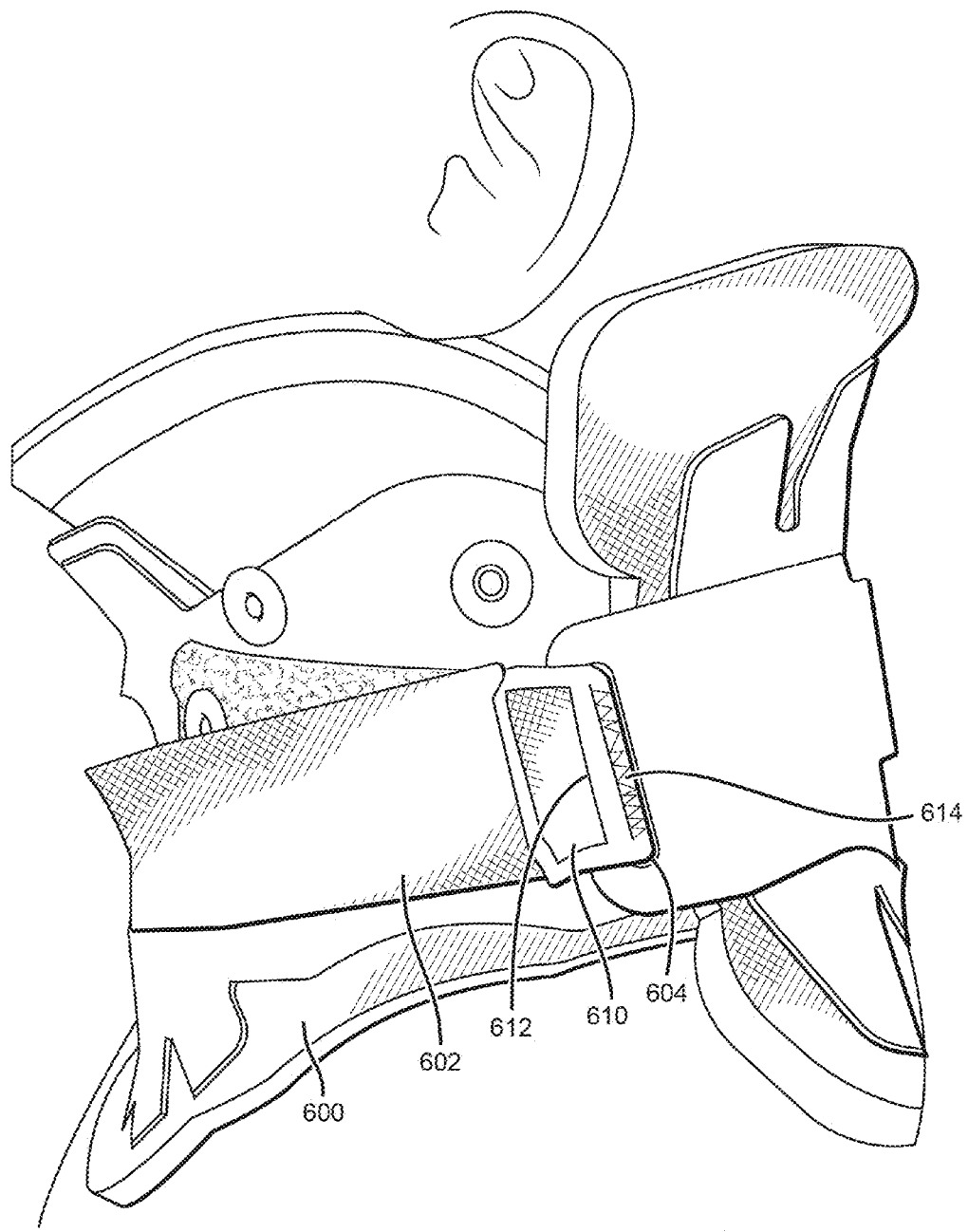
FIG. 6 is a perspective view of a visual tension indicator after the tension in the strap has reached a threshold force.

As embodied in FIG. 2, the second tension indicator 220 comprises differently colored and/or designed portions 222-224 that indicate whether or not a proper amount of tension has been applied to the strap 202. For example, portions 222 and 224 (when viewable) indicate that too little or too much tension, respectively, has been applied to strap 202. In contrast, portion 223 indicates a proper amount of tension has been applied to strap 202. As portions 222-224 are all visible, the tension in the strap 202 has surpassed the second threshold. Use of visual tension indicators to indicate when a proper amount of tension has been applied is also shown in FIGS. 4-6.

Preferred visual tension indicators comprise stretchable (i.e., elastic) portions configured to stretch a defined length per unit of force applied to the stretchable portion. Such visual tension indicators function by having a perceptible difference in color and/or design once tension in the strap reaches a threshold amount of tension. It is contemplated that these stretchable portions could each be disposed between two portions of a strap, such that each stretchable portion couples the two strap portions to thereby form a continuous piece. Preferably, a hook and loop fastener or other commercially suitable fastener(s) can be used to secure one portion of the strap to the other portion. For example, a first portion of the strap can have a plurality of loops that are fastened to a plurality of hooks on a second portion of the strap.

Figure 3:
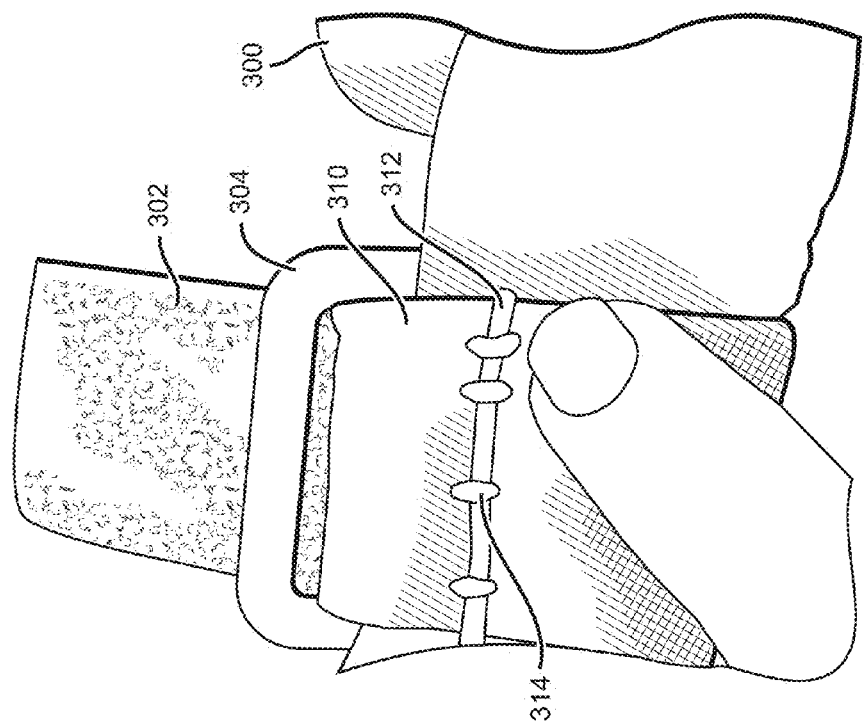
FIG. 3 is a close-up view of a non-visual tension indicator.

In FIG. 3, an orthotic 300 is shown having a strap 302 that tensions and secures orthotic 300. A tension indicator 310 can comprise a raised element 312, which is coupled to strap 302. The raised element 312 can be sewn to the tension indicator 310 using thread 314, although any commercially-suitable fastener(s) could be used. The raised element 312 is preferably disposed such that when the raised element 312 passes through and thereby interacts with a member 304 of the orthotic 300, at least one of (a) a tactile signal and (b) an audible signal can be produced.

Figure 4:
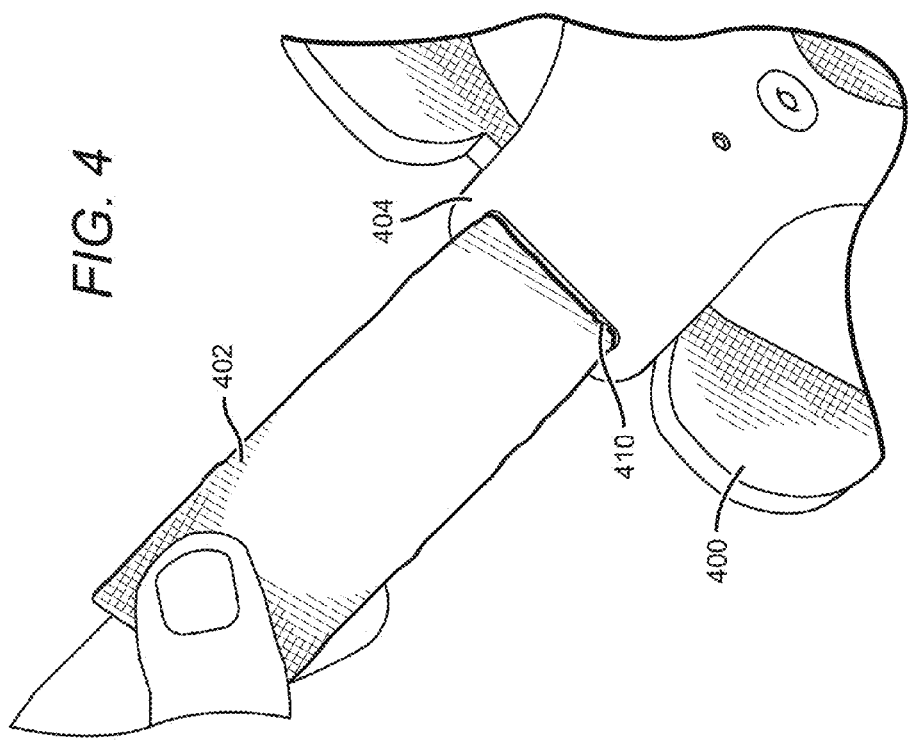
FIGS. 4-5 is a perspective view of a visual tension indicator prior to the tension in the strap reaching a threshold force.

In FIG. 4, an orthotic 400 is depicted having a strap 402 that tensions and secures orthotic 400, in which there is little tension in the strap 402. Strap 402 is fed through a member 404 of orthotic 400. A tension indicator 410 can be coupled to the strap 402 such that a visual signal is produced when the tension in the strap 402 reaches a threshold. FIG. 5 illustrates an orthotic 500 having a strap 502 that tensions and secures orthotic 500, where the tension is less than a defined threshold. Strap 502 can be fed through member 504 of orthotic 500. A tension indicator 510 can be coupled to the strap 502 such that a visual signal is produced when the tension in the strap 502 reaches a threshold.

FIG. 6 illustrates yet another embodiment of an orthotic 600 having a strap 602 that tensions and secures orthotic 600. Strap 602 can be passed by a member 604 of orthotic 600. A tension indicator 610 can be coupled to the strap 602 such that a visual signal is produced by portion 614 when the tension in the strap 602 reaches a first threshold. The display of portion 614 at the member 604 indicates that the proper level of tension has been applied to the strap 602. Should only portion 612 be shown rather than portions 612 and 614, this indicates that the strap 602 is improperly tensioned.

Figure 7:
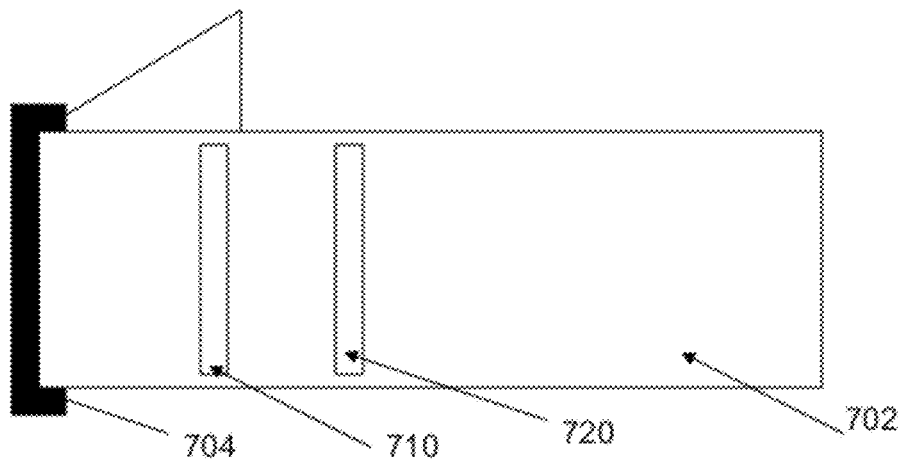
FIG. 7 is a perspective view of first and second tension indicators coupled to a strap.

FIG. 7 illustrates a strap 702 having a first tension indicator 710 that produces at least one of (a) a first tactile signal and (b) a first audible signal when a tension in the strap 702 reaches a first threshold that is less than a permanent deformation threshold. Strap 702 also has a second tension indicator 720 that produces at least one of (a) a second tactile signal and (h) a second audible signal when a tension in the strap 702 reaches a second threshold that is less than a permanent deformation threshold. The respective signals can be produced when each of the tension indicators 710 and 720 interacts with a member 704 of the orthotic 700. The member 704 is preferably rigid and comprises an eyelet, although all commercially-suitable configurations are contemplated such that a tactile and/or audible signal can be produced from the interaction of the tension indicators 710 and 720 with the member 704.

Alternatively, the second tension indicator 720 cart be coupled to a different strap of the orthotic, and produce a signal when the indicator 720 interacts with a second member of the orthotic. Preferably, the second tension indicator 720 is distinct from the first tension indicator 710. It is contemplated that the signal(s) produced by the second tension indicator 720 could be similar to or distinct from the signal(s) produced by the first tension indicator 710. In addition, it is contemplated that the second threshold could be equal to or different from the first threshold.

In some contemplated embodiments, the second tension indicator 720 can comprise a second raised element that is sized and dimensioned to interact with a member 704 of the orthotic 700. In further contemplated embodiments, the first and second tension indicators 710 and 720 can have different sizes and dimensions, such that the tension indicators 710 and 720 can interact with different members of the orthotic 700. Thus, for example, the first tension indicator 710 could have a height that is less than a height of the second tension indicator 720 and less than a height of a first member 704 of the orthotic 700. In this manner, the first tension indicator 710 could pass by the first member 704 without producing a signal, and could then produce a signal when the first tension indicator 710 interacts with a second member (not shown).

Figures 8A, 8B:
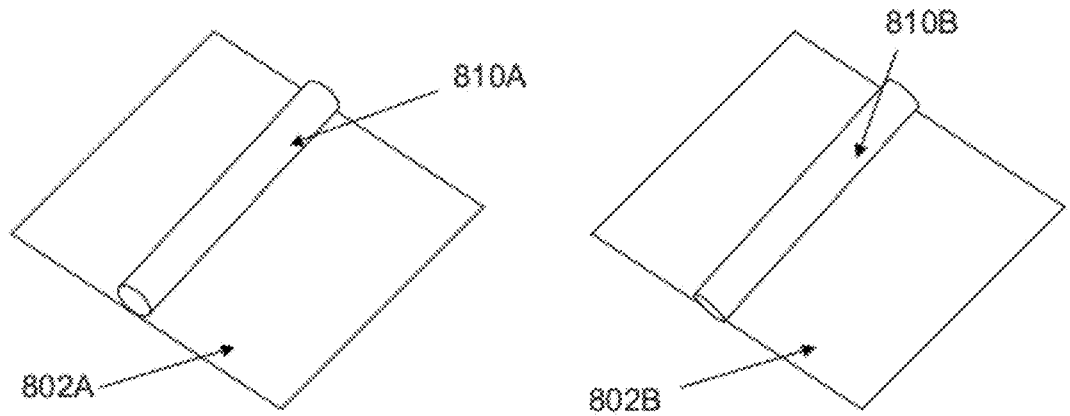
FIGS. 8A-8B are perspective views of a tension indicator in its non-signal and signal states, respectively.

In FIGS. 8A-8B, tension indicators 810A and 810B are coupled to strap 802A and 802B and shown in a non-signal and signal state, respectively.

Figure 9:
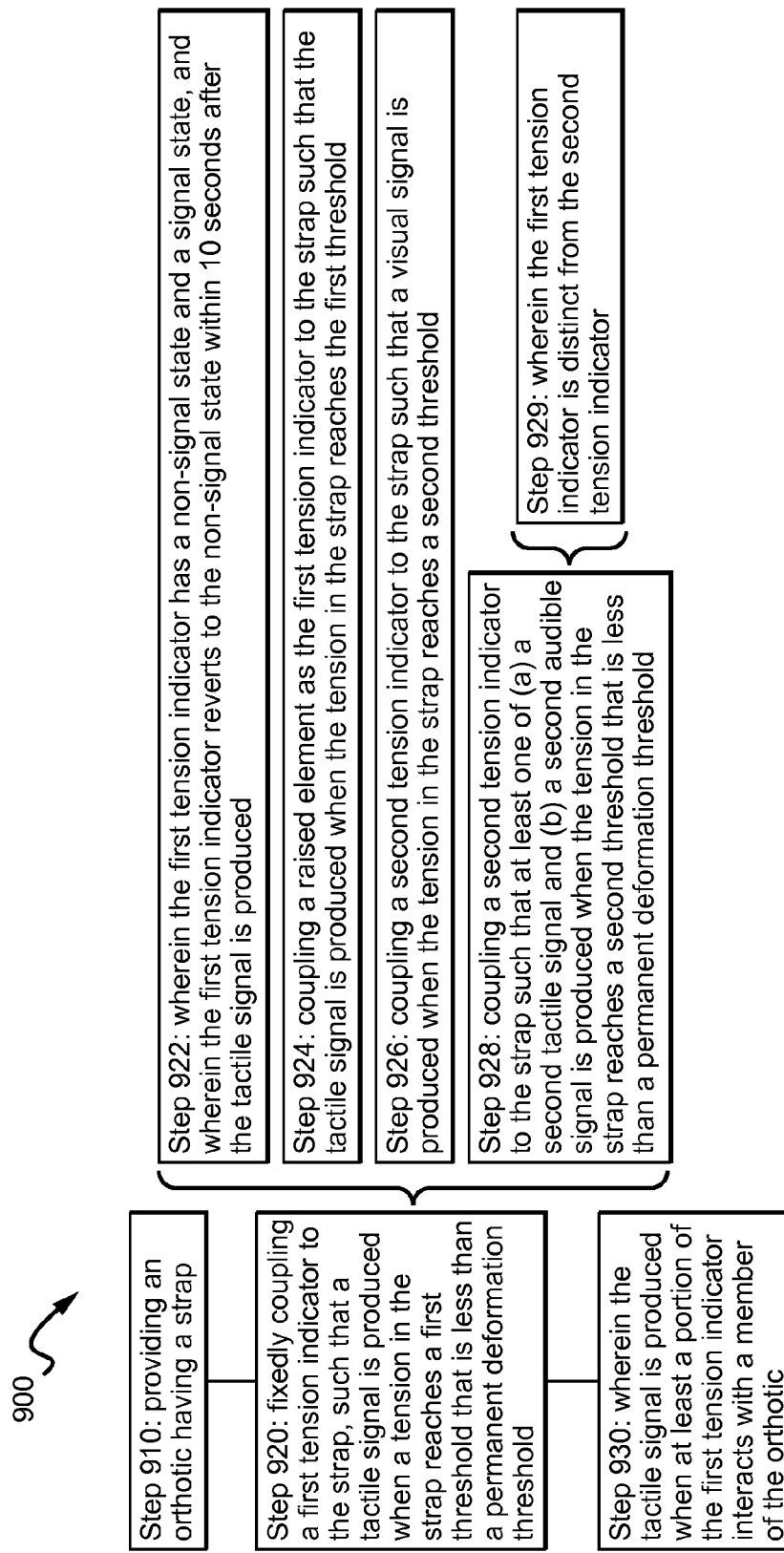
FIG. 9 is a flowchart of a method of indicating a proper level of tension in an orthotic.

FIG. 9 illustrates a method 900 of producing a tactile signal to indicate a proper level of tension in an orthotic strap. In step 910, an orthotic having a strap is provided. A first tension indicator can be fixedly coupled to the strap in step 920, such that at least one of a tactile signal can be produced when a tension in the strap reaches a first threshold that is less than a permanent deformation threshold. In some contemplated embodiments, the first tension indicator can produce both the tactile signal and an audible signal when the tension in the strap reaches the threshold.

In step 922, the first tension indicator can have a non-signal state and a signal state, and the first tension indicator can revert to the non-signal state within 10 seconds after the tactile signal is produced.

In step 924, a raised element can be coupled to the strap as the first tension indicator such that the tactile signal is produced when the tension in the strap reaches the first threshold. The raised element is preferably resilient, and can convert to a signal state during the production of the tactile signal, and revert to a non-signal state within 10 seconds after the signal is produced.

A second tension indicator can be coupled to the strap in step 926, such that a visual signal is produced when the tension in the strap reaches a second threshold. In alternative step 928, a second tension indicator can be coupled to the strap such that at least one of (a) a second tactile signal and (b) a second audible signal is produced when the tension in the strap reaches a second threshold that is less than a permanent deformation threshold. In step 929, the first tension indicator is preferably distinct from the second tension indicator.

in step 930, the tactile signal can be produced when at least a portion of the first tension indicator interacts with a member of the orthotic.

In methods where the first tension indicator produces both a tactile and an audible signal, the signals could be produced at different thresholds.

Figure 10A:
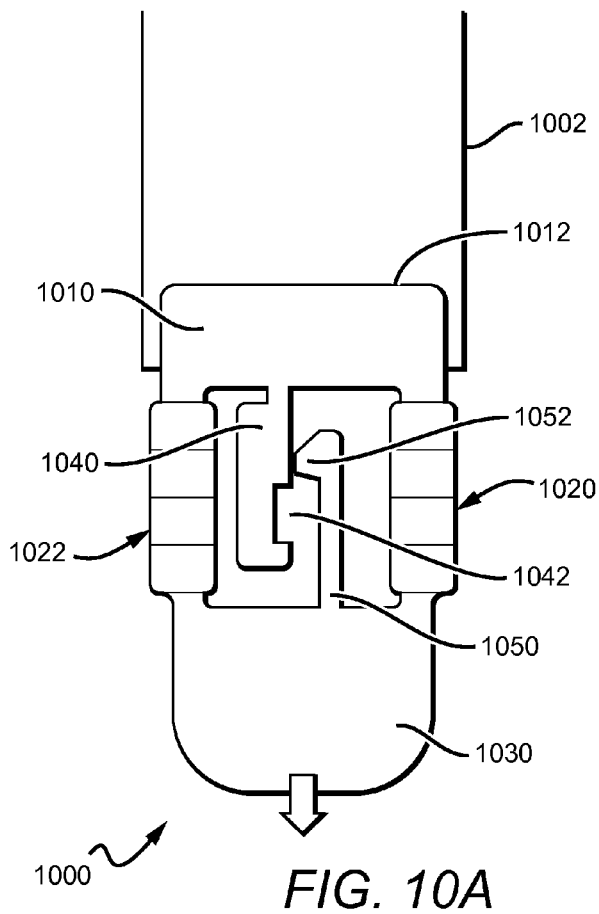
FIGS. 10A-10B are top and perspective views, respectively, of another embodiment of a tension indicator.
Figure 10B:
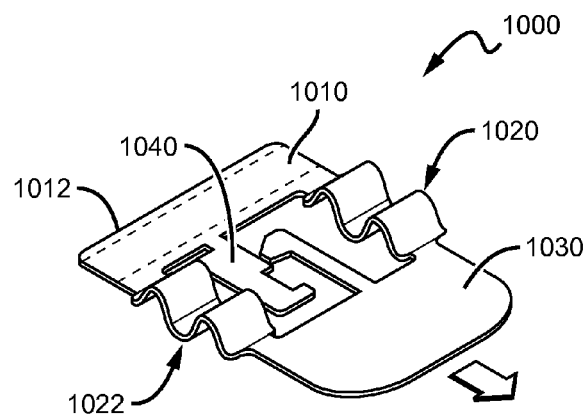

In FIGS. 10A-10B, a tension indicator 1000 is shown that can be coupled to a strap 1002 such that a tactile signal can be produced when tension in the strap 1002 reaches a defined threshold. In preferred embodiments, the tension indicator 1000 is coupled to strap 1002 of an orthotic, although the indicator 1000 could also be used with safety belts and other devices. Preferably, the strap 1002 is inelastic, although it is contemplated that elastic or partially elastic straps could alternatively be used.

Tension indicator 1000 preferably comprises a single, molded piece of material, which could include, for example, a metal or metal composite, a plastic or polycarbonate, and any other commercially suitable material and combination(s) thereof. This advantageously reduces the complexity and cost of manufacturing the tension indicator 1000, as compared with devices having two or more pieces because no assembly is required.

The tension indicator 1000 can include a first portion 1010 that is carried by the strap 1002. The first portion 1010 can include first end 1012 that can be coupled to the strap by any commercially suitable fastener(s), and a second end 1030. In some contemplated embodiments, force can be applied to the second end 1030 such as by pulling the second end 1030 in a direction away from the first end 1012.

The first portion 1010 can also include springs 1020 and 1022, which can couple the first end 1012 to the second end 1030 such that force applied to the second end 1014 can cause one or both of the springs 1020 and 1022 to at least partially flatten, which thereby increases the length of the tension indicator 1000. The tension indicator 1000 can also have a finger 1050 that can include an extended portion 1052, and a catch 1040 configured to interact with the finger 1050 as a function of the tension in the strap 1002. The first portion 1010 preferably is configured to bias positioning of the catch 1040 and the finger 1050 with respect to one another, and more preferably, bias the position of the catch 1040 apart from the position of the finger 1050.

As tension in the strap 1002 increases, the springs 1020 and 1022 can at least partially flatten, which causes movement of the catch 1040 with respect to finger 1050. In this manner, the notch 1042 of the catch 1040 and the extended portion 1052 of finger 1050 can move closer to one another until the extended portion 1052 snaps into the notch 1042, which produces a tactile signal. The tactile signal advantageously allows a user to ensure that the strap 1002 has a proper level of tension, which can be critical especially for orthotics where under or over-tightening of the strap 1002 could harm the orthotic's user.

Depending upon the desired level of tension in the strap 1002, the composition and/or the size and dimension of the tension indicator 1000 could vary.

FIGS. 11A-11D illustrate another embodiment of a tension indicator 1100 having a first portion 1110 that includes first and second ends 1112 and 1130. Springs 1120 and 1122 can couple the first end 1112 to the second end 1130. As force is applied to the tension indicator 1100, such as via the second end 1130, the springs 1120 and 1122 can at least partially flatten, which increases the overall length of the tension indicator 1100. In preferred embodiments, the springs 1120 and 1122 of tension indicator 1100 can revert to their initial positions after the tension in the strap 1102 decreases, which advantageously allows the indicator 1100 to be re-used.

The tension indicator 1100 can also include a finger 1150 that can have an extended portion 1152, and a catch 1140 that optionally has a notched portion 1142. As springs 1120 and 1122 flatten, the extended portion 1152 of finger 1150 can ascend ramp 1144 until the extended portion 1152 reaches an apex of the ramp 1144 as shown in FIGS. 11B-11C. The ascension of the extended portion 1152 can increase a torsion spring force in the extended portion 1152. As the tension in the strap increases to a predetermined threshold, the extended portion 1152 can move from the ramp 1144 to strike the notched portion 1142 of catch 1140, which releases the built-up force in the extended portion 1152 and produces a tactile signal. Catch 1140 can advantageously prevent further forward movement of the extended portion 1152 and thereby prevent further extension of springs 1120 and 1122 if tension in the strap continues to increase beyond the predetermined threshold. This advantageously can prevent permanent deformation of the tension indicator 1100.

Once tension in the strap begins to decrease, the extended portion 1152 and springs 1120 and 1122 can return to their respective initial or non-tensioned positions shown in FIG. 11B.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A tension indicator for a strap, comprising:
   a catch coupled to the strap;
   a finger coupled to the strap, and configured to interact with the catch to produce a tactile signal when tension in the strap reaches a defined amount from an initial slacken configuration of the finger and the catch on the strap; and
   a portion carried by the strap, and configured to bias positioning of the catch and the finger with respect to one another.

2. The tension indicator of claim 1, wherein the portion is configured to bias positioning of the catch apart from the finger.

3. The tension indicator of claim 1, wherein the portion is configured to (a) extend as the tension in the strap increases, and (b) retract as the tension in the strap decreases.

4. The tension indicator of claim 1, wherein the tension indicator has a non-signal state when the tension in the strap is a first amount, and a signal state when the tension reaches the defined amount, and wherein the tension indicator reverts to the non-signal state when the tension in reaches the first amount.

5. The tension indicator of claim 1, wherein the portion comprises a spring.

6. The tension indicator of claim 5, wherein the spring is configured to extend as a function of an increase in the tension.

7. The tension indicator of claim 1, wherein the strap is coupled to an orthotic.

8. The tension indicator of claim 1, wherein the catch, the finger, and the first portion comprise a single piece of material.

* * * * *